United States Patent [19]

Becker

[11] 4,396,016

[45] Aug. 2, 1983

[54] INTRAVENOUS SOLUTION FLOW REGULATOR

[76] Inventor: Karl E. Becker, 4247 Crane Blvd., Jackson, Miss. 39216

[21] Appl. No.: 831,129

[22] Filed: Sep. 7, 1977

[51] Int. Cl.³ .............................................. A61M 5/16
[52] U.S. Cl. ...................................... 604/126; 222/67; 222/481; 222/179; 222/192; 222/399; 222/590; 222/244; 222/252; 222/257
[58] Field of Search ............ 128/214 C, 214 R, 214 E, 128/214.2, 227, 214 D; 222/22, 52, 67, 145, 481; 137/179, 192, 399, 590

[56] References Cited

U.S. PATENT DOCUMENTS

| | | | |
|---|---|---|---|
| 1,205,410 | 11/1916 | Tenney | 128/214 R |
| 2,562,445 | 7/1951 | Butler et al. | 128/214 |
| 2,696,818 | 12/1954 | Van Loghem | 128/214 C |
| 3,216,419 | 11/1965 | Scislowicz | 128/214 R |
| 3,217,711 | 11/1965 | Pecina et al. | 128/214 R |
| 3,227,173 | 1/1966 | Bernstein | 137/192 |
| 3,738,361 | 6/1973 | Price | 128/214 C |
| 3,929,157 | 12/1957 | Serur | 137/453 |
| 3,931,818 | 1/1976 | Goldowsky | 128/214 C |
| 3,949,745 | 4/1976 | Howell | 128/214 C |
| 3,967,620 | 7/1976 | Noiles | 128/214 C |
| 3,989,043 | 11/1976 | Dimeff | 128/214 C |
| 3,999,542 | 12/1976 | Shaw | 128/214 C X |
| 4,013,072 | 3/1977 | Jess | 128/214 C |
| 4,173,222 | 11/1979 | Muetterties | 128/214 C |

FOREIGN PATENT DOCUMENTS

| | | | |
|---|---|---|---|
| 1766980 | 10/1970 | Fed. Rep. of Germany | 128/214 |
| 1171578 | 2/1957 | France | 128/214 |
| 1179425 | 5/1959 | France | 128/214 |
| 914198 | 3/1964 | France | 128/214 |
| 1546081 | 11/1967 | France | 128/214 |
| 2253544 | 4/1975 | France | 128/214 |
| 7704768 | 9/1977 | France | 128/214 |
| 822195 | 10/1959 | United Kingdom | 128/214 C |
| 977039 | 12/1964 | United Kingdom | 128/214 C |
| 990583 | 4/1965 | United Kingdom | 214/ |

Primary Examiner—Kyle L. Howell
Assistant Examiner—Nancy A. B. Swisher
Attorney, Agent, or Firm—Fleit & Jacobson

[57] ABSTRACT

An automatic intravenous flow regulator for regulating the infusion rate of a parenteral solution flowing from an intravenous fluid container to a patient. When the level of parenteral solution in the container is above a threshold level, the infusion takes place at a first flow rate. When the level of fluid in the container drops below the threshold level, fluid flow continues but at a second flow rate less than the first flow rate. The flow rate is controlled principally from outside the IV container; while in a second embodiment, the flow rate is controlled from within the IV container. Other embodiments are disclosed including one in which the initial flow rate may be adjusted; one in which the fluid is filtered prior to delivery to the patient; one in which the initial flow rate is maintained at a constant value with time, secondary flow rate remains fixed, and complete filtration of the intravenous solution being infused is provided.

25 Claims, 10 Drawing Figures

INTRAVENOUS SOLUTION FLOW REGULATOR

BACKGROUND OF THE INVENTION

The present invention relates primarily to a flow regulator for use in a parenteral solution administration set, and more particularly to a flow regulator which sustains fluid flow to the patient at a reduced rate after the level of fluid in the intravenous fluid (IV) container drops below a predetermined threshold, and to a flow regulator which provides accurate regulation of the total flow rate of the intravenous infusion. In one design, in addition to the above stated functions, total flow rate is adjustable and may be maintained very constant over the time of infusion, and complete filtration of the parenteral solution fluid is provided. In another design, the total flow rate is fixed at a maximum level, and minor adjustments to the flow rate are accomplished by changing the height of the IV container relative to the patient.

In my co-pending U.S. patent application, Ser. No. 702,068, filed July 2, 1976, and entitled "Automatic Intravenous Flow Regulator", I explained the desirability of maintaining the flow of parenteral solution for an extended period of time after the IV container becomes empty, and the problems which result when fluid flow ceases. Briefly stated, if the flow of parenteral solution ceases, even for a brief period of time, the intravenous infusion catheter often becomes clotted, necessitating an intravenous catheter or needle change, with the accompanying discomfort to the patient, incurred cost of materials, and loss of employee time.

In my aforementioned co-pending patent application, there is disclosed a mechanism which associates with an IV container, and which maintains fluid flow for a prolonged period of time even when the container is empty. This mechanism includes a reservoir chamber for receiving and storing parenteral solution from the IV container, and a valving arrangement for automatically decreasing the fluid flow rate to a lower secondary rate once the infusion bottle is empty and fluid level in the reservoir drops below a predetermined threshold level.

A main purpose of the present invention is to accomplish reduced fluid flow when the IV container becomes nearly empty, without the necessity for a special reservoir chamber and its associated valving.

Another main purpose of this present invention is to provide accurate flow rate regulation. Flow rate in most intravenous administration sets is regulated by roller clamps or other means of constricting the orifice of the IV infusing tubing to limit the flow of fluid. However, due to "creep" or "cold flow" of the plastic employed in the IV tubing, flow tends to decrease with time and often will decrease as much as 60% of the desired rate within one hour. Such inaccurate flow regulation necessitates frequent monitoring by hospital personnel to maintain the correct flow. This problem not only results in a waste of valuable medical personnel time but also increases the possibility that the intravenous infusion may be stopped prematurely. To solve this long-standing problem, recently many expensive electronic and magnetic monitoring and motorized pumping devices have become available. These devices, although solving to some extent the present problem, are expensive, cost much more than a simple infusion set, and require frequent nursing personnel visits to assure that the devices remain operational.

SUMMARY OF THE INVENTION

The present invention relates to a flow regulator having integral capabilities for prolonging the time of flow of the parenteral solution at a reduced rate, when the level of fluid in the container reaches a certain threshold level. The present invention provides the advantages of a maintained continuous fluid flow without the necessity for adding additional components such as reservoirs or the like to an existing intravenous infusion set.

The inventive flow regulator is adapted for direct mating with a standard IV container. The present invention provides apparatus having a primary, high flow rate fluid path, a secondary, low flow rate fluid path, and a regulator means to cut off the primary fluid flow path to both fluid and air flow when the fluid level in the IV bottle falls below a threshold level.

The flow regulating means can be embodied in different forms incorporating the teachings of the present invention. For example, the flow regulating valving means may be a hydrophilic membrane filter that prohibits the passage of air. The specific configuration of the flow regulator need only be so constructed so as to accomplish the stated purpose of enabling a rapid flow rate of parenteral solution until the level of solution in the IV container reaches a certain lower threshold level, whereupon the fluid flow is then restricted to a lower flow rate, thereby extending the period of time during which the last portion of parenteral solution in the IV container is infused to the patient.

The present invention provides apparatus which performs the flow regulating function and which also has an integral means for accurately controlling the fluid flow rate. In one embodiment of the present invention, accurate and constant primary and secondary flow rate regulation is provided by the use of membrane filters. As is well known, the flow through these filters is proportional to the pore size of the filter, the effective surface area of the filter, and the fluid pressure head as determined by the height of the infusion fluid level relative to the plane of the patient. These parameters may be chosen such that the present invention provides a conventional intravenous flow rate which will change only one to two percent per hour of infusion. And in fact, this change in flow rate is caused almost entirely by the decrease in the height of the intravenous infusion solution from the continued infusion.

The present invention provides apparatus employing several means for easily adjusting this flow rate, for example, by changing the effective area of the filter membrane, or by changing the height of the IV infusion container relative to the patient, or both. In any event, the flow resulting from the use of the present invention is much more constant and easier to regulate than the conventional IV infusion sets which use clamps or the like to regulate and control the flow by restricting the feed tubing inner diameter. In addition, the present invention also provides apparatus which is adapted to completely filter the intravenous fluid which is being infused to the patient. Accordingly, it may be seen that the principal objectives of the present invention are to extend the time duration of IV infusion to a patient when the IV container becomes nearly empty, to accurately regulate the rate of flow of the IV infusion fluid, and to perform both of these objects in a single integral device and to provide such device with means to provide complete filtration of the IV infusion fluid.

Therefore, it is a main object of the present invention to provide an intravenous flow regulator which automatically extends the time during which parenteral fluid flows to a patient when the infusion bottle becomes nearly empty.

It is still a further object of the present invention to provide a flow regulator for an IV container, which flow regulator includes valving means adapted to reside external to the IV container when in use.

A more specific object of the present invention is to provide an intravenous flow regulator having a primary flow path which is intended to deliver the parenteral solution to the patient when the IV container has an adequate fluid supply and having a mechanism for closing this primary path to air and fluid entry once the fluid level in the IV container reaches a predetermined threshold level, and employing a secondary reduced rate flow path which is solely responsible for the infusion to the patient after the threshold level has been reached.

A still further specific object of the present invention is to provide an intravenous flow regulator having a continuously active secondary flow path which becomes the sole source of infusion fluid when the primary flow path has been closed.

It is another main object of the present invention to provide an intravenous flow regulator which accurately regulates intravenous flow rate.

It is another object of the present invention to provide an intravenous flow regulator providing accurate and continuously maintained flow rate regulation and employing a filter membrane of selected effective surface area and pore size thereby providing a fixed flow rate commensurate with typical intravenous infusion flow rates.

It is still a further object of the present invention to provide an intravenous flow regulator having a primary filter membrane and including a means for adjusting the effective surface area of the membrane presented to the fluid, thereby providing accurate flow rate adjustment.

It is still a further object of the present invention to provide an automatic flow regulator employing a mechanism for limiting the flow to a predetermined fixed maximum when the IV container is relatively full and for automatically reducing the fluid flow to a predetermined lower flow rate when the IV container is almost empty.

It is another object of the present invention to provide an automatic intravenous flow regulator having primary high flow rate, and secondary low flow rate fluid paths, and having a primary membrane filter of selected pore size located therein with means to adjust the surface area of the membrane for principally determining the primary flow rate, and having a secondary filter membrane of selected pore size and surface area for determining secondary flow rate and having a mechanism for closing off the primary fluid path to the passage of fluid when the IV container becomes nearly empty, and utilizing the hydrophilic quality of the primary and secondary membranes to block the passage of air through these membranes when they are no longer in contact with fluid and utilizing also the filtration properties of the membrane to completely filter the IV fluid infused to the patient.

Still another object of the present invention is to provide an intravenous flow regulator having a primary membrane filter of selected pore size and effective surface area so as to provide an IV flow rate commensurate with typical IV infusions and to provide filtration of particles and bacteria, and having a secondary membrane filter of selected pore size and effective surface area to provide a low flow rate and to provide particle and bacteria filtration and having a means for stopping flow through the primary membrane when the level of fluid in the IV container reaches a predetermined threshold level.

These and other objects of the present invention, as well as many of the attendant advantages thereof, will become more readily apparent when reference is made to the following description, taken in conjunction with the accompanying drawings.

DETAILED DESCRIPTION OF THE DRAWINGS

Figures 1, 2:
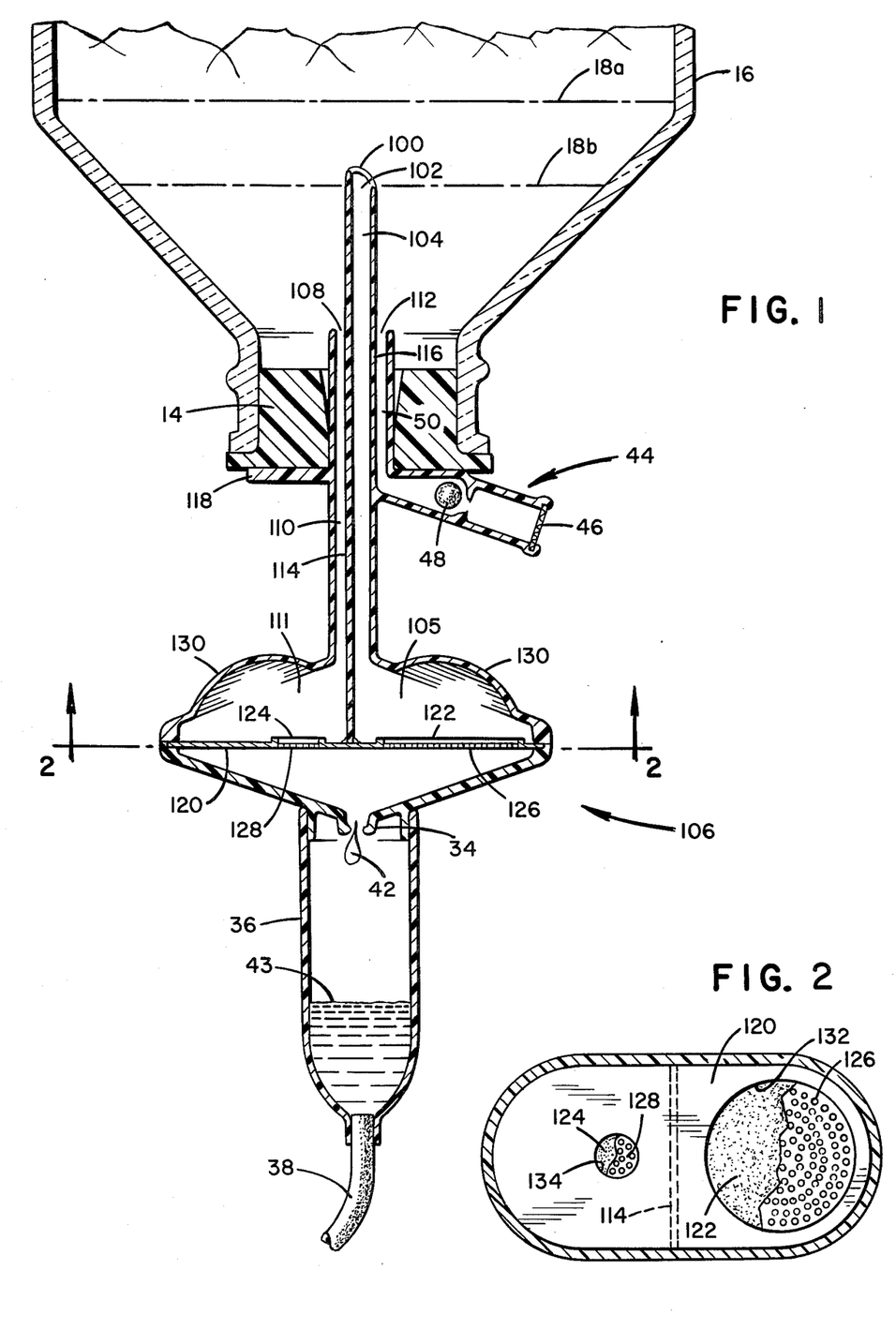
FIG. 1 illustrates another embodiment of the present invention inserted in an IV container.
FIG. 2 is a cross section of the embodiment of FIG. 1, taken along site line 2—2.

FIG. 1 is an embodiment of the present invention. In this embodiment the filtering, valving, and flow regulating mechanisms are located primarily exterior to the IV container. In the embodiment of FIG. 12, a piercer is provided and has a sharp tip 100 for piercing the IV container stopper or diaphragm. Arranged proximate this tip 100 is the primary flow path inlet 102, through which the IV fluid flows into the primary fluid path 104. This fluid path then continues down the piercer shaft and into a primary flow chamber 105 on the right side of the body portion of the flow regulator, which is shown generally as 106.

Located further down the piercer shaft at a positon slightly above the IV container stopper innermost surface is a secondary fluid inlet 108, through which the IV fluid may enter and flow into a secondary fluid path 110. The second fluid path 110 then continues down the piercer shaft and into the secondary flow chamber 111 located on the left side of the body portion 106 of the flow regulator. Also formed at part of the piercer shaft is an air outlet 112, which is part of the air entry system 44, which will be required in any rigid or nonvented IV container. A septum 114 is formed by the construction of the various flow paths and serves to separate the primary fluid path 104 and chamber 105 from the secondary fluid path 110 and its respective chamber 111. Similarly, a septum 116 separates the primary fluid path 104 from the air entry system 44 to prevent communication therebetween. A stop 118 is provided towards the lower part of the shaft of the piercer and encircling the shaft of the piercer so as to allow accurate positioning of the piercer in the IV container. The stop 118 is intended to abut the outer portion of the bottle stopper or diaphragm 14. Inside the body portion of the flow regulator 106 is a membrane carrier element 120 which has mounted therein, as well as sealed thereto, a primary flow regulator and hydrophilic filter membrane 122. A secondary flow regulator and hydrophilic membrane filter 124 is also mounted in and sealed to the membrane carrier element 120. If necessary, the membrane carrier 120 can be provided with supports for the membranes such as the fenestrated membrane supports 126 and 128, which will be shown in more detail hereinbelow. Also provided in the flow regulator body 106 are two compressible domes, shown typically at 130, which are compressed after the inventive device has been inserted into an IV container in order to vent the air in the system out of the inlet 102 and 108, thereby permitting fluid to enter the primary fluid path 104 and chamber 105, as well as the secondary fluid path 110 and chamber 111. Such fluid then serves to wet the filter membrane 122 and 124 and thus to permit the flow of fluid to the patient.

Referring now to FIG. 2 the membrane carrier 120 of FIG. 1 is shown in more detail. As mentioned above, both the primary 122 and secondary 124 membrane filters are hydrophilic membranes, and these membranes, shown partially cut away in FIG. 2 are positioned on the top surface of the membrane carrier 120 and are sealed thereto. Optional support means may be provided to support the primary and secondary membranes from beneath. Such supports may comprise fenestrated or strutted support surfaces 126 and 128 which can be incorporated as part of the membrane carrier element 120. These support surfaces are designed to support the membranes without restricting fluid flow therethrough. Therefore, the effective areas of the membranes are set by the sizes of the apertures 132 and 134 in the carrier element 120, and not by the area of the fenestrations in the support surfaces. It should be noted that, in regard to the support surfaces 126 and 128, certain of the membranes which are now commercially available are provided with a nylon mesh or other supporting backing, in which case the support structures 126 and 128 would not be necessary. The septum 114 which separates the primary flow path 104 and secondary flow path 110 continues the length of the piercer and abuts the top surface of the membrane carrier 120 in such a manner as to seal thereto. In this way, the separation between the primary and secondary fluid paths and chambers is accomplished.

Additionally, although the embodiment of FIGS. 1 and 2 discloses the membranes in a circular form such form is not a necessity in order to successfully practice the present invention. The membranes may take any convenient shape, with the only constraint being a suitable surface area exposed to the fluid and a suitable membrane pore size so as to provide the desired flow rate.

The operation of the flow regulator as embodied in FIGS. 1 and 2 will now be described. Initially, the stopper 14 of a fresh IV container 16 is pierced with the tip 100 of the piercer and the inventive device is fully inserted into the IV container until it reaches the stop 118. The IV container is then inverted and placed on a conventional support stand. The domes 130 are alternately compressed and released, thereby forcing air out of the primary and secondary chambers 105, 111, up the primary and secondary paths 104, 110 and then into the IV container. The release of the domes draws fluid down the primary and secondary flow paths 104, 110 and into the primary and secondary chambers 105, 111, thereby wetting the filter membranes 122, 124, making the membranes permeable to the fluid. Once the membranes are wet and the air has been removed from the primary and secondary paths, the drip chamber 36 is compressed and an IV tubing clamp provided in the system is closed. This serves to draw fluid through the membranes and down into the drip chamber. At that time the tubing clamp is released and the fluid flows down the IV tubing 38; when the fluid flows out the end of the tubing the device is connected to a suitable IV catheter which has already been placed in the patient. As shown above, a roller clamp located on the IV tube 38 may then be adjusted to provide the required infusion rate.

On the exhaustion of the supply of fluid in the IV container 16 the inventive piercer is removed and simply inserted into a fresh IV container. The domes 130 are once again compressed and released so as to purge any air from the secondary and primary fluid paths and to allow fluid to enter the chambers. Since the membranes will not pass air, fluid will still remain in the IV set distal to the membranes and thus no priming of this part is required. Therefore, the device is ready for use with another fresh IV container.

In operation, when the fluid supply is generally at level 18a or higher, fluid enters both the primary fluid path and the secondary fluid path and flows through the respective membranes 122, 124 into the drop chamber 36 and thence to the patient. Since membrane 122 has a pore size and surface area permitting a high flow rate when the fluid is at level 18a or above, fluid flow rate is adjusted and regulated by a tubing clamp or the like located on IV tube 38. However, once the fluid level falls to 18b, fluid no longer enters primary fluid inlet 102 and the sole source of the infusion is through the secondary inlet 108. The pore size and surface area of secondary membrane 124 are chosen so as to limit the fluid flow to a low rate, that is, a rate sufficient to prevent clotting of the intravenous catheter. Additionally, the length of the piercer is such that sufficient fluid will remain in the IV container when the fluid level is at 18b, so as to provide about one to two hours of continued infusion at the secondary flow rate. Since both membranes 122, 124 are hydrophilic and do not pass air once they have become wet, the membranes 122, 124 will perform a valving function by nature of their hydrophilic qualities and the position of the primary and secondary fluid inlets. Additionally, air will not enter the drip chamber through either membrane, thus preventing the possibility of air emboli to the patient. Also, the membranes provide a filtering function since all of the IV fluid infused into the patient must pass through either the primary or the secondary membrane before it reaches the patient.

Figures 3, 5A, 5B:
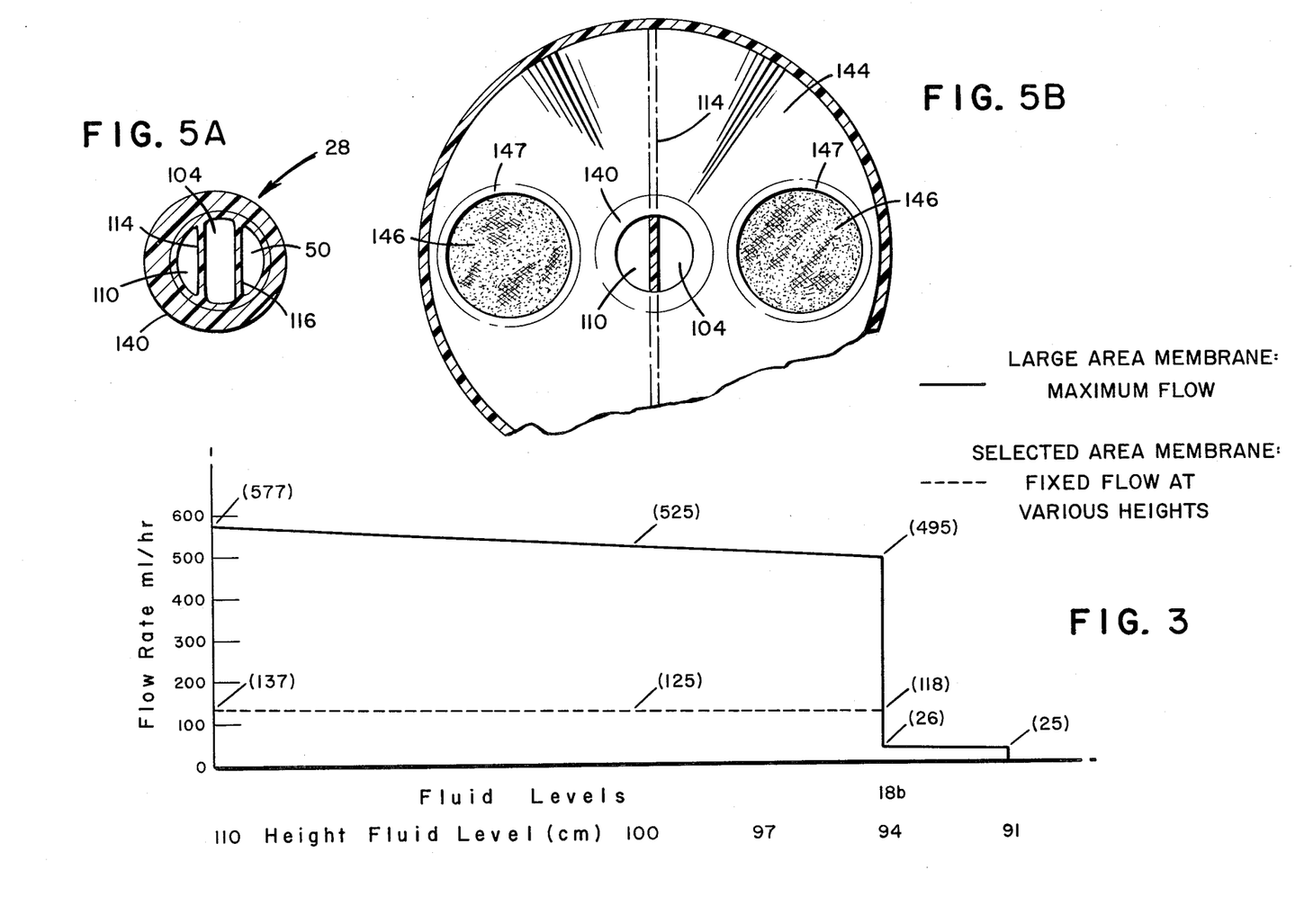
FIG. 3 is a graph of the parenteral solution flow pattern utilizing the embodiment of the present invention illustrated in FIG. 1.
FIG. 5A is a cross section of the embodiment of FIG. 4, taken along site line 5A—5A.
FIG. 5B is a cross section of the embodiment of FIG. 4, taken along site line 5B—5B.

The flow pattern of the FIG. 1 regulator is illustrated in FIG. 3. Fluid flow rate declines abruptly when the fluid reaches the threshold level 18b. This is because the entire primary membrane will be exposed to air at one time when air enters the fluid inlet 102 and proceeds down the fluid path 104 and into primary chamber 105. For example, using a Millipore 0.22 micron filter, type MF, having a 378 mm² area for the primary membrane 122 and a 19 mm² area for the secondary membrane 124, a maximum flow rate (shown in solid line) of approximately 525 ml per hour is possible when the IV fluid level is approximately 100 cm above the patient and above level 18b. This is four times greater than the usual IV flow rate. In any event, once the liquid fluid level falls to level 18b the flow rate will decrease automatically to only about 25 ml per hour.

It may be seen that by choosing the correct dimensions of the embodiment of FIG. 1, the inventive flow regulator may easily regulate both the primary and secondary flow rates and therefore avoid the use of inaccurate tubing clamps which would be necessary in a system which could deliver 525 ml per hour. For example, using a Millipore 0.22 micron, type MF, filter membrane only 76 mm² for the primary membrane and 19 mm² for the secondary membrane, and assuming the typical infusion height of 100 cm, a total flow rate (shown in dashed line) of only about 125 ml per hour will be provided when the fluid level is above 18d. The fluid rate will then drop to 25 ml per hour when the fluid level is below 18b. This type of flow regulation is much more accurate and stable than that which may be provided by the use of a tubing clamp or the like and, in the present inventive flow regulator, the set flow rate will decrease only approximately one to two per cent per hour. Additionally, as mentioned above, the flow rate may be easily and accurately adjusted simply by raising or lowering the IV container relative to the patient and thereby changing the fluid pressure head.

Figure 4:
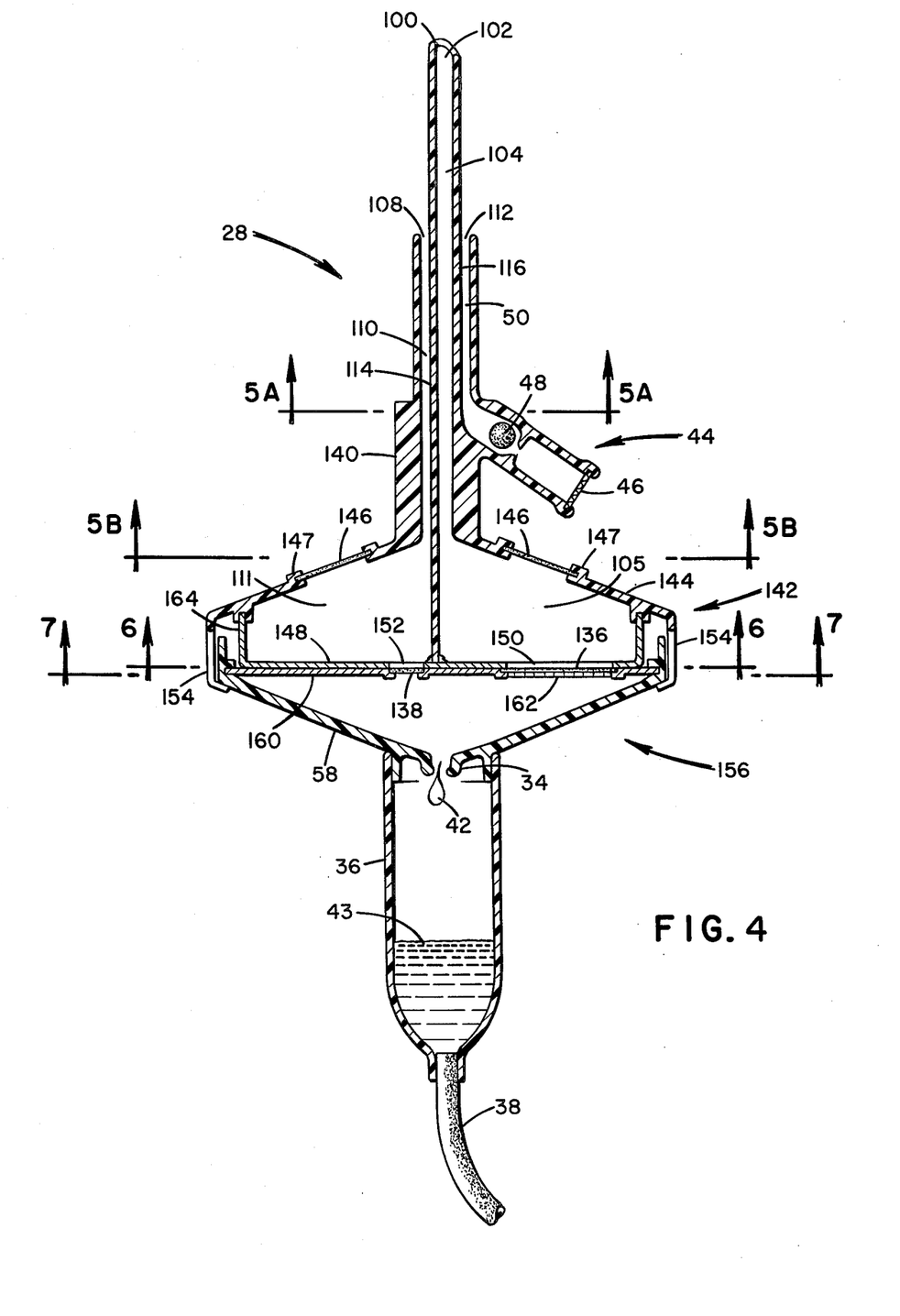
FIG. 4 illustrates another embodiment of the present invention.

FIG. 4 is another embodiment of the inventive flow regulator and piercer wherein the filtration and flow regulation apparatus are located exterior to the IV container. In this embodiment, the flow regulation and filtration unit is essentially circular and is constructed of a top and bottom portion arranged so as to permit the two pieces forming the body to rotate in relation to each other. In this way, as will be described below, the flow is regulated by changing the effective surface area of the primary membrane. The piercer body 28 is provided once again with a sharp tip 100 for piercing the IV container stopper, and located adjacent this sharp tip is a primary fluid inlet 102 which permits fluid to flow into the primary fluid path 104 and subsequently into the primary chamber 105. The fluid then is passed by the primary membrane filter 136 before being introduced to the patient. Located at a point further down the piercer shaft 28 from the primary fluid inlet 102 is a secondary inlet 108 which permits fluid to enter and flow down the secondary fluid path 110 thence into the secondary chamber 111. Once again a secondary filter membrane 138 is provided in the fluid path prior to it being fed to the patient. A septum 114 separates the primary and secondary fluid paths and chambers. An air entry system 44 is provided in this embodiment which is identical to that shown in the embodiment of FIG. 1. The piercer body 28 has a portion having a larger diameter 140 so as to form a shoulder which then may abut the IV bottle stopper or diaphragm. This serves to set the amount of penetration of the piercer into the IV container. As mentioned above, the body of the inventive flow regulator is provided with an upper portion shown generally at 142 which includes an outer housing surface 144 within which are fixed two hydrophobic membrane filters, shown typically at 146 and sealed in place by sealing rings 147. These hydrophobic membranes 146 will allow the venting of air out of the primary and secondary flow paths and chambers and thereby permit the fluid to enter the primary and secondary flow paths and chambers in order to wet the respective membranes. Additionally, the upper portion of the flow regulator 142 is provided with a flow regulating plate 148 which has a primary fluid aperture 150 and a secondary fluid aperture 152. Flow regulation plate 148 is sealed to the septum 114 so that primary and secondary fluid paths and chambers will remain separated at all times. A circumferential locking lip arrangement shown typically at 154 is provided in order to keep the upper body portion 142 permanently attached to the lower portion, which is shown generally at 156. The lower portion 156 has outer walls 158 which serve to collect the fluid and channel it to the drip chamber 36 which is attached to the outer walls of the lower portion. Also mounted in the lower portion 156 is a membrane carrier 160, which forms a liquid tight seal with the flow regulating plate 148. Primary membranes 136 and secondary membrane 138 are mounted in slight recesses in the membrane carrier 160 and are sealed therein. These membranes are so fixed such that a flat surface will be formed with the upper surface of the membrane carrier 160. Additionally, beneath membrane 136, membrane carrier 160 has formed as an integral part a membrane support 162 which serves to support the membrane 136 yet allow the passage of fluid therethrough. The lower portion 156 is formed with a circumferential raised lip 164 which projects up into the upper body portion 142 and is intended to coact with a corresponding lip 154 of the upper portion 142 so as to aid in forming a liquid-tight seal. If necessary, an O-ring or similar gasket might be provided at this interface so as to assure a positive liquid-tight seal. However, the sealing of the upper portion 142 with the lower portion 156 must be made in such a manner so that the two body portions may rotate relative to one another, since it is this rotation which permits the regulation of the flow rate. The operation of the rotation and the manner in which such rotation produces a variable flow rate capability is better seen in FIGS. 16 through 20.

FIG. 5A is a cross section of the inventive flow regulator taken along site line 5A—5A of FIG. 15. The main body of the piercer 28 includes the portion of increased diameter 140 which forms the shoulder for abutting against the IV container stopper. The septums 114 and 116 separate the primary path 104 from the secondary path 110 and from the air entry channel 50.

FIG. 5B is a cross section taken along site line 5B—5B which is located where the piercer body 28 joins the upper portion 142 of the flow regulator. Accordingly, the enlarged diameter portion 140 of the piercer body may be seen as well as a portion of the dividing septum 114. The remainder of the septum 114 is shown in phantom since it is located beneath the top surface 144 of the upper portion. The hydrophobic membranes 146 may be sealed in place by the use of sealing rings 147. As mentioned, these hydrophobic membranes are intended to pass air but not fluid and thereby serve to vent the air from the piercer and the upper body of the device when it is first inserted into an IV container.

Figure 6:
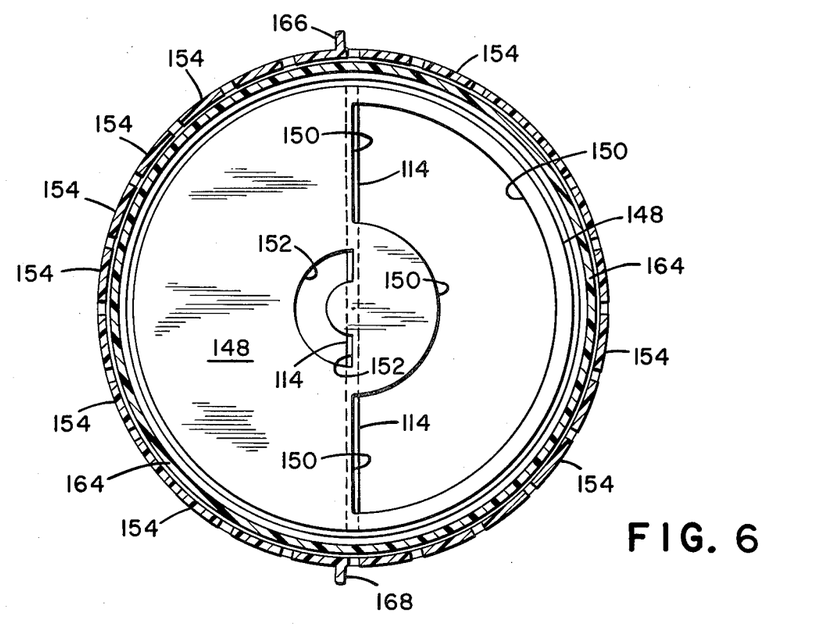
FIG. 6 is a cross section of the embodiment of FIG. 4, taken along site line 6—6.

FIG. 6 is a cross section of the embodiment of FIG. 15 taken along site line 6—6 and which shows the flow regulating plate 148. The flow regulating plate 148 is located inside the upper portion 142 and is an integral part of the flow rate mechanism of the embodiment of FIG. 15. The flow regulating plate is formed as the bottom surface of the upper body portion 142 and is intended to mate closely with the top of the membrane carrier 160 which is formed in the lower body portion 156. These two parts 148 and 160 are intended to be in as close a relationship as possible so as to form fluid-tight and air-tight seals between the solid parts of these plates. The flow regulating plate 148, as shown in FIG. 6, is a solid plate except for semicircular primary flow aperture 150 and a semicircular secondary flow aperture 152. Septum 114 is seen in cross section and separates the two sides of the compression plate 148 which correspond to the primary and secondary chambers. Additionally, lip 164 of the lower body portion 156 is seen located between the outer rim of the flow regulating plate 148 and the interlocking lip structure 154 of the upper body portion 142. The interlocking lip 154 is slotted at its outer edges in several places so as to permit it to expand outwardly when it is inserted over the lower body portion 156 during the manufacturing process. Tabs 166 and 168 are affixed to lip 154 and serve to interact with a similar tab or stop on the lower body portion 156 which thereby serve to limit rotation of the upper body on the lower body to approximately one half turn.

Figure 7:
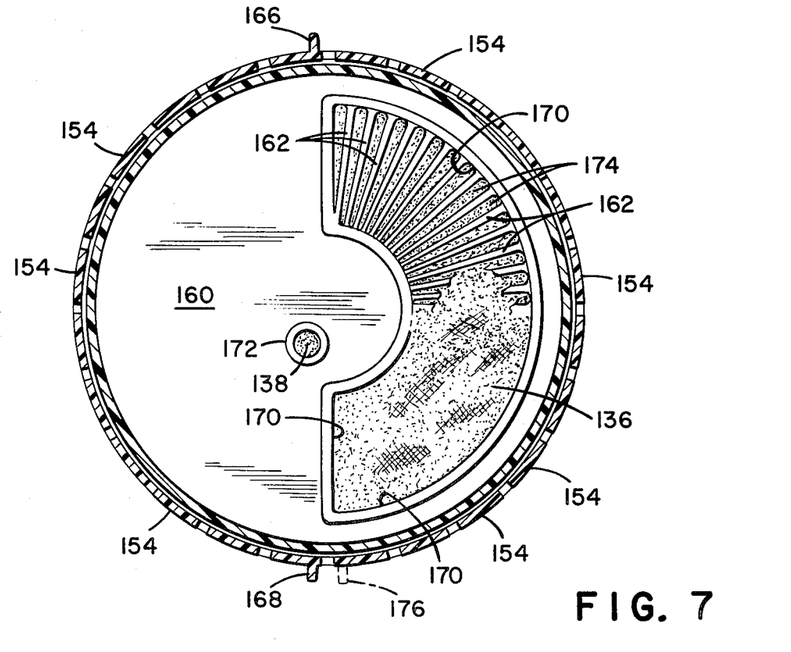
FIG. 7 is a cross section of the embodiment of FIG. 4, taken along site line 7—7.

FIG. 7 shows the membrane carrier 160 of FIG. 4 and is a cross section taken along site line 7—7 which is just below the section referred to in FIG. 17. The primary and secondary membranes 136 and 138 are shown located in their respective positions and having the majority thereof cut away from clarity of this figure. The primary membrane 136 is semicircular in shape and fits into a shallow recess 170 which is in the shape of the primary membrane. Additionally, support struts 162 project under the primary membrane 136 so as to lend it support and to keep it from deforming or sagging. The fluid flows pass the primary membrane and through the openings 174 which are formed between the adjacent struts 162. The primary membrane 136 may be sealed to the primary membrane support rim 170 and to the membrane support struts 162 by a suitable FDA approved adhesive, solvent, or heat seal. The primary membrane 136 is recessed only enough so that the upper surface is flush with the topmost surface of the membrane carrier 160. Similarly, secondary membrane 138 is recessed in a flush relationship and sealed to the support rim 172. A tab or stop 176 projects from the side wall 158 of the lower body portion 156. This stop cooperates with the stops 166 and 168, shown in FIG. 6, to limit the direction and the amount of rotation of the device.

In operation, the flow regulating plate 148 is rotated on the membrane carrier 160 to regulate the flow rate through the primary fluid membrane. This rotation of the upper body and hence the flow regulating flow plate 148 upon the lower body portion and the membrane carrier 160 serves to move the primary flow aperture 150 such that it is no longer directly in alignment with the primary membrane 136. Instead, part of membrane 136 will be covered tightly by the solid portion of the flow regulating plate 148 thereby affecting the effective surface area of the primary membrane which is exposed to the fluid. Since flow rate is proportional to the effective area of the membrane filter, the flow rate is thereby accurately regulated by this rotation. In the embodiment described, complete rotation of 180° of the upper portion relative to the lower portion of the flow regulator will completely shut off the flow, since upon complete rotation both the primary and the secondary membranes will be completely covered by solid portions of the flow regulating plate 148.

In the embodiment of FIG. 7, the membranes were recessed to provide a smooth upper surface of the membrane carrier 160. An alternate embodiment is to use one large membrane which would cover and be sealed to the entire upper surface of membrane carrier 160. In this manner, fluid could flow only through the membrane where there exist openings beneath it. Thus the devices would be functionally equal. It should be noted that in covering the entire surface with the membrane, ease of manufacture is provided as well as the additional feature that the membrane itself could act as a gasket to effect a fluid-tight seal between the movable plates 148 and 160.

Figure 8:
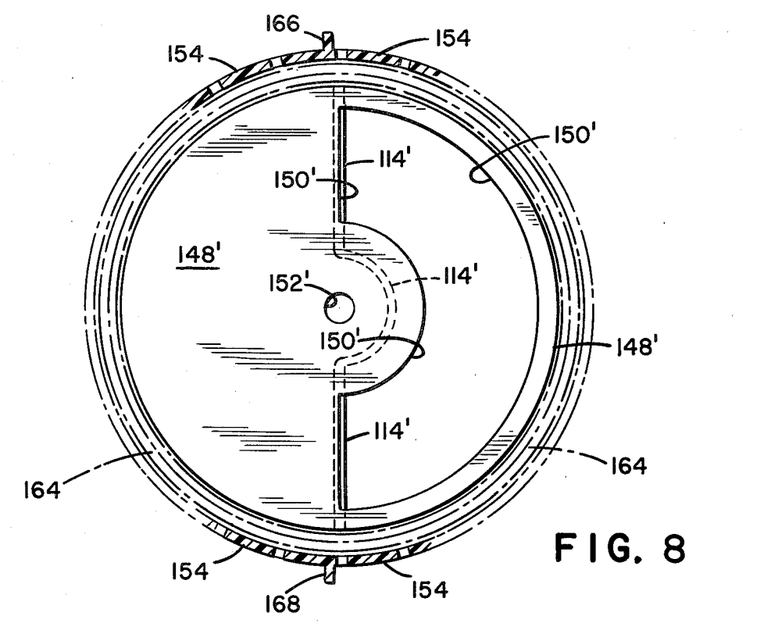
FIG. 8 is an alternate embodiment of the baffle, or flow regulator plate shown in FIG. 6.

FIG. 8 is a another embodiment of the flow regulating plate of FIG. 6. In this embodiment the primary flow of aperture 150' is similar to that shown in FIG. 6. However, the secondary flow path aperture 152' is now located in the center of the flow regulating plate 148'. Because of this relocation of the secondary flow path aperture 152', the septum 114' must be relocated in its relation to the plate surface. Accordingly, septum 114' deviates around the central aperture 152', so as to provide a continuous separation of the primary and secondary chambers. In all other aspects, this embodiment of the flow plate 148' retains all of the structure features as discussed relative to the plate of FIG. 6.

Figure 9:
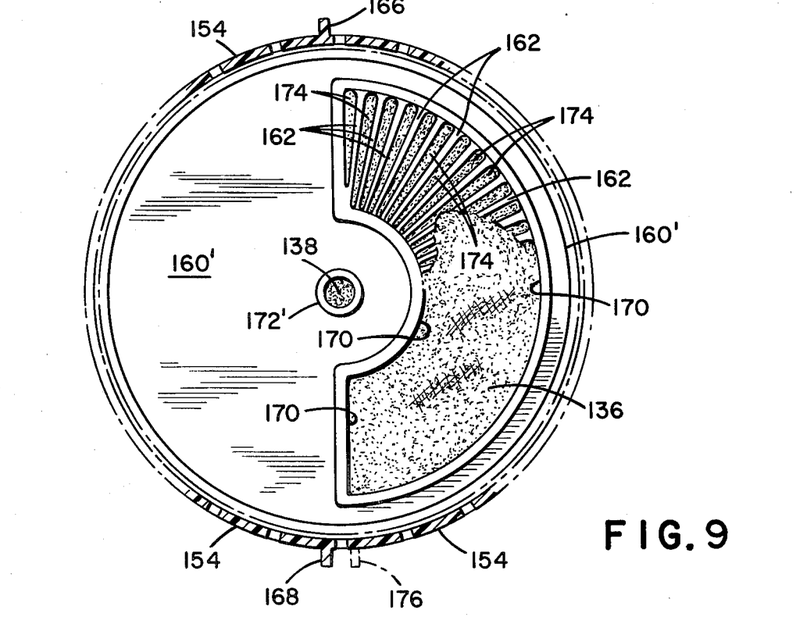
FIG. 9 is an alternate embodiment of the membrane carrier shown in FIG. 7.

FIG. 9 is the companion alternate embodiment of the membrane carrier of FIG. 7. This alternate embodiment is intended to cooperate with the flow regulating plate of FIG. 8. The primary membrane 136 is semicircular in shape and is affixed to a recessed support rim 170 which is provided in the membrane carrier 160'. In order to describe this embodiment the major portion of the primary membrane 136 has been shown cut away. Again the same support struts 162 are provided in this embodiment. This primary membrane 136 is therefore sealed such that the fluid can then flow through the membrane and out the multiple openings 174 which are provided between adjacent support struts 162. In this embodiment however, the secondary membrane 138 is generally circular in shape and is mounted in a recessed support rim 172' which is centrally and axially located in the membrane carrier 160'. The secondary membrane 138 has been shown partially cut away so as to better show the manner in which the embodiment is assembled.

In operation, the flow regulating plate 148' of FIG. 8 is mounted directly upon and in contact with the membrane carrier 160' which has the appropriate filter membranes mounted thereon. Upon rotation of plate 148' on 160' the solid portion of plate 148' will cover a part of the surface of the membrane 136 mounted on membrane carrier 160' and thereby change the effective surface area of the primary membrane, thereby acting to regulate the flow. However, rotation of the device will not affect the effective area of the secondary membrane, since it is centrally located and is in registry with the aperture in the regulating plate. Thus, flow rate through the secondary membrane will be at all times constant and uninterrupted when the portions of the flow regulator are mutually rotated. Therefore, the tabs or stops as shown in FIGS. 6 and 7 are not necessary in this embodiment but have been included only to indicate the relative effective surface area of the primary membrane of this embodiment.

The operation of the embodiment of FIG. 4 will now be described. Initially, the piercer 28 is inserted fully into an IV container until it is limited by the stop provided by the increased diameter portion 140. In this position, secondary inlet 108 will be located just inside the IV container and just above the end of the stopper. The IV container is then inverted and supported on a conventional stand above the patient in the typical manner. Air is vented from the upper body portion 142 of the device through the hydrophobic membranes 146 and fluid flows down the primary and secondary flow paths 104, 110 into the primary and secondary chambers 105, 111 and thence through the primary and secondary flow apertures 150, 152. Prior to insertion into the container the upper body 142 should be rotated on the lower body portion 156 so that the flow regulator is adjusted for maximum flow. The IV fluid then wets the membranes 136 and 138. The drip chamber 36 is compressed, and the IV tubing 38 is closed; thus fluid is drawn through the membranes and into the drip chamber 36. The IV tubing 38 is then released and fluid flows down the tubing. When the fluid flows out the distal end, the device is ready for insertion into an IV catheter which has been placed in the patient. Flow rate through the device is now at a maximum and it may be adjusted to the desired flow rate by counting the drops formed at the drop former 34 and rotating the upper body portion 142 on the lower body portion 156, until the desired rate is achieved. The present invention will maintain the flow rate which has been set with only a one to two percent decrease per hour which is due to the falling of the pressure head of the fluid due to the continued infusion. The flow rate may be readjusted at some later time to a desired rate by again rotating the upper body portion 142 relative to the lower body portion 156 or it may be adjusted by increasing the height of the IV container above the patient.

The flow will continue at approximately the chosen rate until the IV container is almost empty, at which time the fluid will no longer be above the primary inlet 102 and the primary membrane 136 will no longer be exposed to fluid. At this time the sole source of infusion is the secondary membrane 138 whose pore size and area are so chosen to limit the infusion to a slow rate. The IV will continue for an extended period of time at this slow rate, until the IV bottle is changed or until the IV bottle becomes completely empty, at which time the infusion stops. Since the primary and secondary membranes are hydrophilic and will not pass air, no air will be permitted to enter the lower body or drip chamber or IV tubing thus avoiding the possibility of air emboli. Additionally, at the time a fresh IV container is added air is vented from the piercer and upper body automatically through the hydrophobic membranes 146; fluid enters the chambers and rewets the membranes and the device once again starts flowing at the set, desired infusion rate. It should also be noted that the use of the primary and secondary membrane provides complete filtration of the IV fluid used in the infusion.

Typically, the primary membrane is selected so that the effective surface area and pore size provide a maximum flow rate of from 500 to 1000 ml per hour and the secondary membrane provides a flow rate of approximately 15 to 35 ml per hour. Also, the length of the piercer as well as the placement of the primary and secondary inlets are chosen so that about 25 to 50 ml remain in the IV container when the primary inlet is no longer exposed to the fluid. This provides an extended infusion of approximately 1 to 2 hours. For example, an Acropor, 0.45 micron, membrane filter from Gelman Instrument Company having an effective surface area of 396 $mm^2$ being used as the primary membrane will provide a flow rate of approximately 1000 ml per hour at an infusion height of 100 cm. Depending on the particular configuration of the embodiment, the support struts 162 decrease the effective area by about one half and therefore allow a maximum flow through this membrane of about 500 ml per hour. It should be noted that the support struts of the embodiment of FIG. 4 are in fact flow limiting, since the membrane is affixed to the support struts. The fenestrated supporting structures 126, 128 of the embodiment shown in FIG. 2 are not flow limiting since the membranes are not affixed to the support structures. An Acropor, 0.45 micron, membrane filter having an area of 10 $mm^2$ utilized as a secondary membrane provides a flow of about 25 ml per hour when the infusion level is approximately 91 to 95 cm above the patient. Therefore, total maximum flow through the device is approximately 525 ml per hour. By rotating the device 45°, the flow will decrease to about 375 ml per hour; 90° to about 250 ml per hour; and 135° to about 125 ml per hour. Further rotation decreases the flow further. If the embodiments of FIGS. 6 and 7 are used, flow may be shut off completely by rotating the device 180°. In the embodiment of FIGS. 8 and 9 the flow decreases to a minimum of only about 25 ml per hour, since fluid continues to flow through the secondary flow path located in the center of the device.

Finally, as may be appreciated, the device illustrated in FIGS. 1 and 4 might be made with only a primary flow path and with no secondary flow path or associated secondary flow path elements such as inlets, membranes, apertures, etc. In this manner, the device functions simply as a flow regulator and provides none of the extended period of infusion at the time the IV container becomes nearly empty. Of course, the device will still filter the fluid and prevent the possibility of air emboli entering the patient. Additionally, such device would not have to be made integrally with a piercer but may have a fitting for mating with a distal end of an IV set and an outlet for associating with a short length of IV tubing for inserting into a suitable IV catheter. The device would still act as a flow regulator and filter but would not be positioned next to the IV container. Such device would then not only filter the IV container fluid but also any fluid or medications introduced downstream from the IV container. Furthermore, it should be appreciated that the present invention contemplates regulating flow from an IV container by using filters to set maximum possible flow rate. In this regard, typical infusion rates are generally in the neighborhood of between 100 and 150 ml/hr. A filter having a preselected area and pore size can effectively set maximum flow, with great accuracy, anywhere within this typical range.

It should be understood that the specific embodiments of the present invention as described above have been presented for the purposes of illustration only and without any intention of limiting the scope of the present invention. Accordingly, it is an intention that the present invention be limited not by the above, but only as defined in the appended claims.

What is claimed is:
1. An automatic flow regulator for delivering a fluid such as a parental solution from a fluid source to a patient, the flow regulator comprising: a body portion having an inlet for receiving fluid from said fluid source, an outlet for delivering fluid to said patient, and a flow path for delivering fluid from said inlet to said outlet; a tubular elongated piercer extending from said body inlet portion co-axial with said inlet adapted to extend into said fluid source having a primary fluid inlet at the free end of said piercer remote from said body portion and a secondary fluid inlet positioned between said primary fluid inlet and said body portion, said tubular piercer and said inlet forming at least one piercer flow path for delivering fluid entering said primary and secondary fluid inlets to said body portion inlet, said inlets being positioned on said tubular piercer, whereby when said piercer is in said fluid source and is in communication with said fluid said primary fluid inlet defines a threshold level at which fluid flows from said source to said outlet through said primary and secondary fluid inlets at a first flow rate and, when the fluid in said source reaches a certain level, the flow of fluid from said primary inlet is discontinued; and regulating means in said flow path in said body for preventing the flow of air from said primary fluid inlet to said outlet when the level of said fluid in said source falls below said primary inlet level, whereby enabling fluid to flow from said source to said outlet through only said secondary fluid inlet at a second flow rate less than said first flow rate.

2. The flow regulator recited in claim 1 wherein said piercer extends into the interior of said source a preselected distance so that when said primary inlet level is reached by the fluid a quantity of fluid remains in said fluid source sufficient to continue fluid flow at said second flow rate for a time between one and two hours.

3. The flow regulator recited in claim 1, wherein said first flow rate is approximately 100–150 ml/hr.

4. The flow regulator recited in claim 1, wherein said second flow rate is such that fluid flow will continue for approximately one to two hours after said threshold level is reached by the fluid.

5. The flow regulator recited in claim 1, and further comprising a drop forming means and an air-fluid interface for enabling the monitoring of the rate of fluid infusion into a patient.

6. The flow regulator recited in claim 1, and further comprising a filter membrane in the fluid path of said secondary fluid inlet having a preselected surface area and pore size for determining said second flow rate and for blocking the passage of air from said secondary fluid inlet to said outlet.

7. The flow regulator recited in claim 6, wherein said means comprises a filter membrane which passes fluid but not air, and which has a surface area and pore size so that said first flow rate is approximately 100–150 ml/hr.

8. The flow regulator recited in claim 1, wherein said means comprises a filter membrane which passes fluid but not air.

9. The flow regulator recited in claim 8, wherein said filter membrane has a surface area and pore size which determine a primary flow rate equal to said first flow rate less said second flow rate.

10. The flow regulator recited in claim 1, and further comprising an air inlet means for allowing air to enter said source as fluid leaves said source through said primary and secondary fluid inlets.

11. The flow regulator recited in claim 1, and further comprising hydrophilic membrane filters in the respective fluid paths of said primary and secondary fluid inlets for providing complete filtration of all parenteral fluid supplied to the patient from said source.

12. The flow regulator recited in claim 1, wherein said body portion is an integral extension of said piercer.

13. The flow regulator recited in claim 1, wherein said at least one piercer flow path comprises first and second piercer flow paths, communicating, respectively, with said primary and secondary fluid inlets; and further comprising primary and secondary chambers for receiving fluid from said respective first and second piercer flow paths; and primary and secondary membranes mounted in said respective primary and secondary chambers.

14. The flow regulator recited in claim 13, wherein said primary and secondary membranes are hydrophilic membrane filters; and wherein the surface area and the pore size of said respective primary and secondary membranes determines said first flow rate.

15. The flow regulator recited in claim 13, wherein said secondary membrane is a hydrophilic membrane filter, and wherein the surface area and pore size of said secondary membrane determine said second flow rate.

16. The flow regulator recited in claim 13, and further comprising regulator means for affecting the effective surface area of said primary membrane.

17. The flow regulator recited in claim 16, wherein said regulator means comprises a flow regulating plate, and wherein the relative position between said flow regulating plate and said primary membrane determines the effective surface area of said primary membrane and hence the primary flow rate equal to said first flow rate less said second flow rate.

18. The flow regulator recited in claim 17, wherein said flow regulating plate is adapted to block all fluid flow through said primary and said secondary membranes.

19. An automatic flow regulator for delivering a fluid such as a parenternal solution from a source to a patient, the flow regulator comprising: a body for receiving fluid from the source, said body having an inlet and a tube extending therefrom co-axial with said inlet adapted to extend into said fluid source, piercing means at the free end of said tube for associating with said source and for delivering fluid from said source to said body, said body having an outlet means at an opposite side for delivering fluid from said body to the patient; primary delivery means within said body communicating with said tube and said outlet means and said piercing means for delivering fluid from said source to the patient at a first flow rate; means in said tube for stopping delivery of fluid from said source to the patient at said first flow rate upon the fluid in said source reaching a predetermined threshold level; a first liquid permeable and air impermeable membrane in the path of said primary delivery means, between said source and the patient, for blocking the passage of air when the level of fluid in said source falls below said threshold level; secondary delivery path means within said tube including a body and said piercing means for delivering fluid from said source to the patient at a second flow rate which is less than said first flow rate; and a second liquid permeable and air impermeable membrane in the fluid path of said secondary delivery means, between said source and the patient, said second membrane being of preselected surface area and pore size for defining said second flow rate and for blocking the passage of air from said source to the patient.

20. The flow regulator recited in claim 19, wherein said first membrane has a preselected area and pore size for defining said first flow rate.

21. The flow regulator recited in claim 20, and further comprising flow regulating means for varying said first flow rate by varying the area of said first filter membrane which is exposed to said fluid.

22. An automatic flow regulator for use with a closed container supplying parenteral solution to a patient, the flow regulator comprising: a tubular means having at one free end thereof a pointed piercing means; a primary aperture in said tubular means proximate said pointed piercing means adapted to extend into a closed said container; a secondary aperture in said tubular means spaced at a predetermined distance from said pointed piercing means and said primary aperture adapted to extend into said container; a hollow body associated with said tubular means opposite said pointed end and adapted to be arranged external to said container, said hollow body having an inlet co-axial with said tubular means, said hollow body communicating with said primary and secondary apertures; and flow regulator means in said hollow body having a first portion communicating with said primary aperture for permitting solution to pass therethrough at a first flow rate, and having a second portion communicating with said secondary aperture permitting solution to pass therethrough at a second flow rate which is substantially less than said first flow rate.

23. The flow regulator of claim 22, and further comprising a first membrane filter arranged within said first portion of said hollow body such that said solution in said first portion passes only through said first membrane filter; and a second membrane filter arranged within said second portion of said hollow body such that said solution in said second portion passes only through said second membrane filter.

24. The apparatus of claim 23, and further comprising a first hydrophobic membrane located in the external surface of said first portion of said hollow body for permitting air to pass therethrough and for preventing solution to pass therethrough; and a second hydrophobic membrane located in the external surface of said second portion of said hollow body for permitting air to pass therethrough and for preventing solution to pass therethrough.

25. The apparatus of claim 23, and further comprising first and second collapsible domes positioned in a top exterior surface of said hollow body and being constructed to be manually deformed so as to reduce the volume inside said hollow body.

* * * * *